United States Patent
Lombardo et al.

(10) Patent No.: US 8,162,978 B2
(45) Date of Patent: Apr. 24, 2012

(54) NON-METALLIC KNOTLESS SUTURE ANCHOR

(75) Inventors: Giuseppe Lombardo, New Port Richey, FL (US); Steven E. Fitts, Largo, FL (US)

(73) Assignee: Linvatec Corporation, Largo, FL (US)

( * ) Notice: Subject to any disclaimer, the term of this patent is extended or adjusted under 35 U.S.C. 154(b) by 751 days.

(21) Appl. No.: 12/079,097

(22) Filed: Mar. 25, 2008

(65) Prior Publication Data

US 2009/0248068 A1    Oct. 1, 2009

(51) Int. Cl.
*A61B 17/04* (2006.01)
(52) U.S. Cl. ........................................ 606/232
(58) Field of Classification Search ............... 606/53, 606/232, 300, 301, 313; 623/13.11, 13.14; 411/999, 21, 22
See application file for complete search history.

(56) References Cited

U.S. PATENT DOCUMENTS

| | | | | |
|---|---|---|---|---|
| 5,643,321 A * | 7/1997 | McDevitt | ...................... | 606/232 |
| 5,702,215 A * | 12/1997 | Li | ................................. | 411/21 |
| 6,200,329 B1 * | 3/2001 | Fung et al. | .................... | 606/232 |
| 6,695,844 B2 * | 2/2004 | Bramlet et al. | ................. | 606/66 |
| 6,840,953 B2 * | 1/2005 | Martinek | ...................... | 606/232 |
| 6,932,834 B2 * | 8/2005 | Lizardi et al. | ................. | 606/232 |
| 7,497,053 B2 * | 3/2009 | Nicolet | ............................. | 52/161 |
| 7,588,587 B2 * | 9/2009 | Barbieri et al. | ............... | 606/232 |
| 7,637,926 B2 * | 12/2009 | Foerster et al. | ............... | 606/232 |
| 7,837,710 B2 * | 11/2010 | Lombardo et al. | ............ | 606/232 |
| 8,057,524 B2 * | 11/2011 | Meridew | ....................... | 606/321 |
| 2006/0116719 A1 * | 6/2006 | Martinek | ...................... | 606/232 |
| 2006/0235413 A1 * | 10/2006 | Denham et al. | .................. | 606/72 |
| 2007/0270907 A1 * | 11/2007 | Stokes et al. | .................. | 606/232 |
| 2009/0069847 A1 * | 3/2009 | Hashiba et al. | ............... | 606/232 |
| 2009/0099598 A1 * | 4/2009 | McDevitt et al. | ............. | 606/232 |

* cited by examiner

*Primary Examiner* — Corrine M McDermott
*Assistant Examiner* — Todd J Scherbel
(74) *Attorney, Agent, or Firm* — Timothy D. Evans; Gene Warzecha

(57) ABSTRACT

A knotless suture anchor for deployment in a preformed bone hole to secure soft tissue to bone. The suture anchor comprises a hollow outer member and a hollow inner member longitudinally movable within the outer member. Suture is directed along a tortuous path distally through the lumens of both the inner and outer members, transversely across an eyelet situated at the distal end of the inner member and proximally through the lumens of both the inner and outer members. A suture-locking mechanism engaged the suture-locking mechanism by moving the inner member proximally relative to the outer member is provided along the tortuous path to crimp the suture by placing the anchor in a suture locked configuration. The inner member is provided with radially outwardly extending prongs which pass through slots in the outer member in order to engage bone surrounding the bone hole.

17 Claims, 13 Drawing Sheets

US 8,162,978 B2

NON-METALLIC KNOTLESS SUTURE ANCHOR

BACKGROUND OF THE INVENTION

1. Field of the Invention

The invention relates to suture anchors for securing sutures and other filamentary material to soft tissue. More particularly, the invention relates to suture anchors for securing sutures and similar filamentary material to soft tissue to reattach the soft tissue to bone. Still more particularly, the invention relates to suture anchors for knotlessly securing suture and filamentary material at a surgical site.

2. Description of the Prior Art

In situations where ligaments or other soft tissue are being secured to bone, a suture anchor is commonly employed. The anchor is generally inserted into a preformed hole in the bone and a suture or similar filamentary material extends from the anchor and is attached to the soft tissue to be secured to the bone. As used herein, the term "suture" includes monofilament or multi-filament suture as well as any other metallic or non-metallic filamentary or wire-like material suitable for performing the function of a suture including both absorbable and non-absorbable materials.

Whether such surgical procedures are done open or closed, in most instances, the suture must be tied to the soft tissue so that a knot must be formed. When such procedures are done arthroscopically or endoscopically (i.e. closed), creation of a knot is somewhat difficult. As a result, knotless suture anchors have been recently developed to avoid the knot tying step.

One example of a knotless suture anchor is shown in U.S. Pat. No. 6,692,516 (West Jr. et al.) assigned to the assignee hereof and incorporated by reference herein. This patent discloses an expandable metallic knotless suture anchor, the design of which is difficult to implement with the use of non-metallic material. As used herein, the term "expandable" means the diameter of the device increases when it is deployed/anchored in the bone.

U.S. Published patent application 2005/0055052 (Lombardo et al.) discloses a knotless suture anchor which may be made of bioabsorbable material. This application is assigned to the assignee hereof and incorporated by reference herein. While the design disclosed in this reference is compatible with bioabsorbable material, the design is a press-fit design and is limited in the types of surgical procedures for which it is suitable. As used herein the term "press-fit" means the diameter of the device is substantially the same before and after deployment/anchoring in the bone.

In developing a knotless suture anchor for use in rotator cuff repairs, as well as other surgical procedures, it is preferable to assure that the anchor is provided with means to secure it to cancellous bone and means to limit any tendency to migrate above the level of the humeral head or other bone at the anchor site. An expandable design is preferable.

It is accordingly an object of this invention to produce a knotless suture anchor suitable for repairing a rotator cuff and re-attaching it to the humeral head.

It is another object of this invention to produce a non-metallic suture anchor suitable for knotlessly securing suture to attach a first body tissue to a second body tissue.

SUMMARY OF THE INVENTION

These and other objects of this invention are achieved by the preferred embodiment disclosed herein. This invention is a knotless suture anchor comprising a generally cylindrical hollow outer tubular member having a first axial lumen, an outer surface, a distal end and a proximal end and an elongated, generally hollow inner member having a second axial lumen, a proximal end and a distal end, the distal end having a transverse passage for receiving suture therethrough. The inner member is adapted to move longitudinally within the outer member between a distal, suture-unlocked position and a proximal, suture-locked position. A suture is directed along a path distally through the first and second lumens, transversely through the transverse passage, and proximally through the first and second lumens. A suture-locking means is situated along the path proximally of the transverse passage and comprises at least one crimping area interposed between the inner and outer members. The crimping area is normally situated in a suture-unlocked configuration wherein the inner member is situated distally relative to the outer member so the suture is slidable along the path. The crimping area is adapted to be activated into a suture-locked configuration upon proximal movement of the inner member relative to the outer member. The anchor further comprises means for moving the inner member proximally from the suture-unlocked position to the suture-locked position whereby the suture will be crimped between the inner and outer members. A locking means is provided to lock the inner member to the outer member to maintain the anchor in the suture-locked position.

DESCRIPTION OF THE PREFERRED EMBODIMENT

Figure 1:
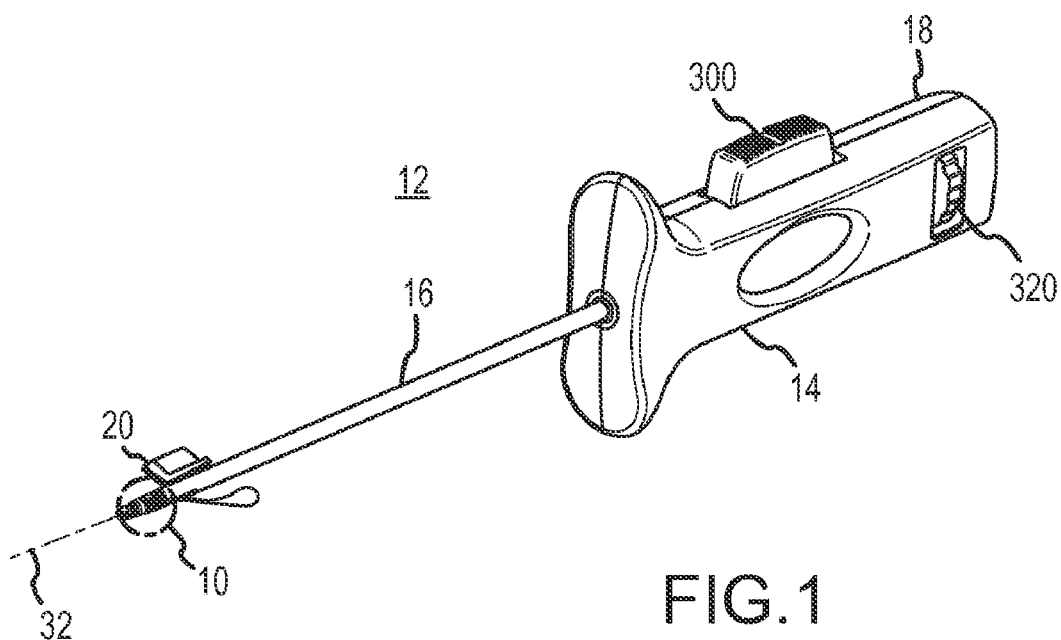
FIG. 1 shows a front perspective view of a knotless suture anchor constructed in accordance with the principles of this invention attached to an inserter for using and deploying the suture anchor.

The knotless suture anchor 10 constructed in accordance with the principles of this invention is shown in FIG. 1. To facilitate its use, anchor 10 is situated at the distal end of an anchor driver or inserter 12 having a handle 14 and an elongated shaft 16 extending distally from the handle. The knotless suture anchor inserter 12 has a proximal end 18 and a distal end 20. The structure and operation of inserter 12 will be discussed below with reference to FIGS. 9 and 10. Anchor 10 is designed to be implanted into a preformed hole (not shown) made in bone at the repair site, and can be used in open or closed surgical procedures.

Figure 2:
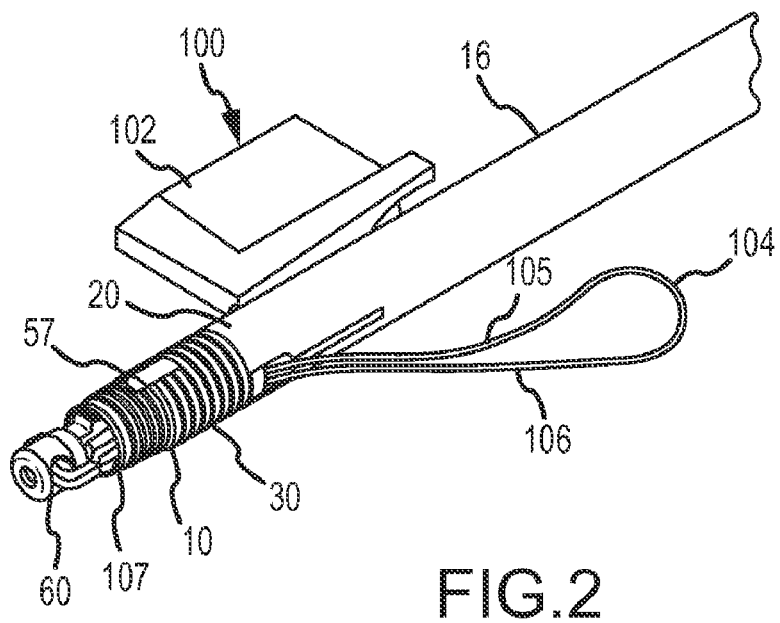
FIG. 2 shows a front perspective view of the distal portion of FIG. 1.
Figure 3:
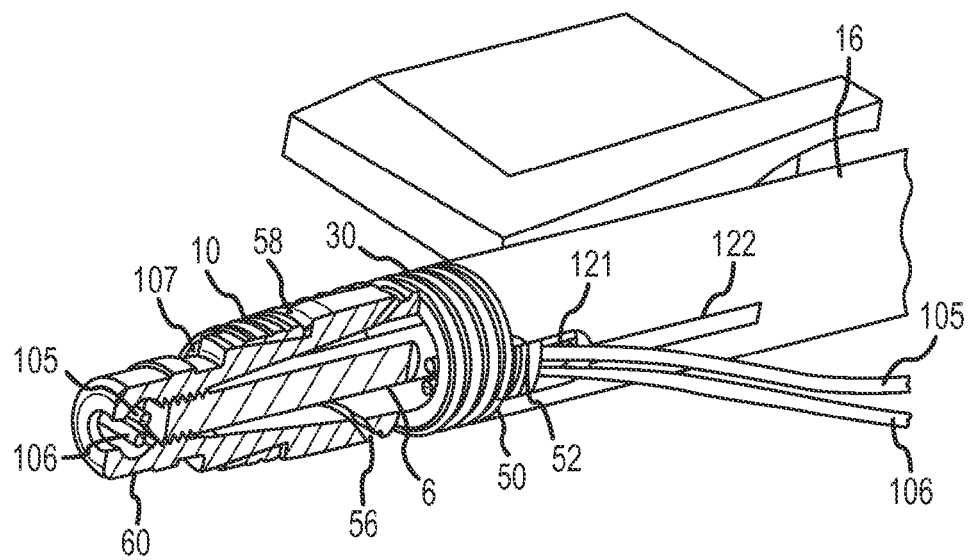
FIG. 3 shows a cut-away view of FIG. 2.
Figure 4:
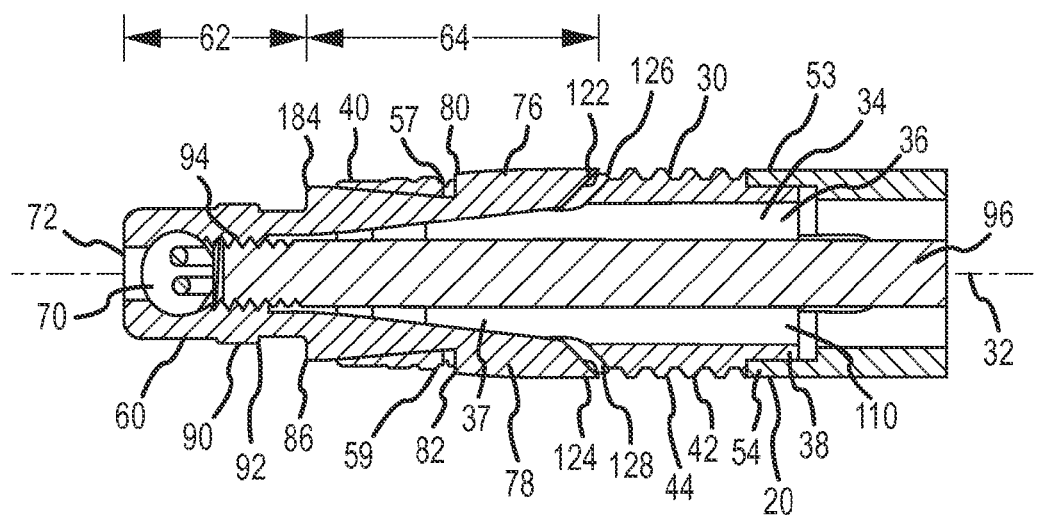
FIG. 4 shows a cross-sectional view of a portion of FIG. 2 with loading filaments partially removed.
Figure 5:
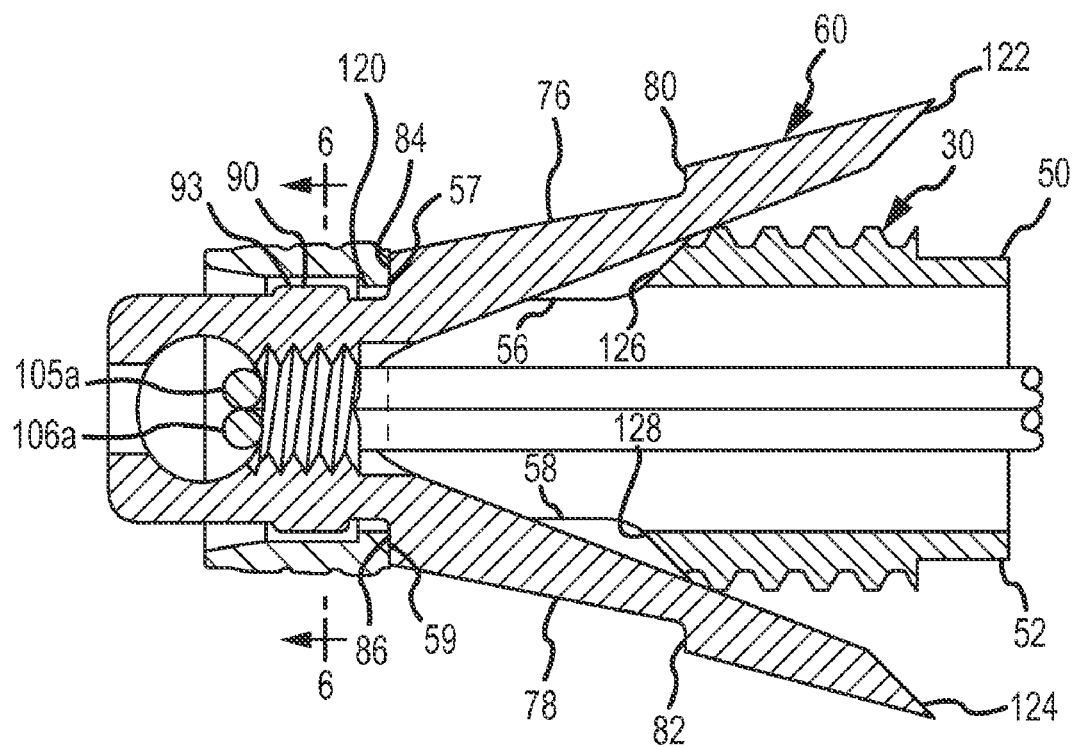
FIG. 5 shows a cross-sectional view of the knotless suture anchor of FIGS. 1-4 in a deployed and suture-locked configuration.
Figure 6:
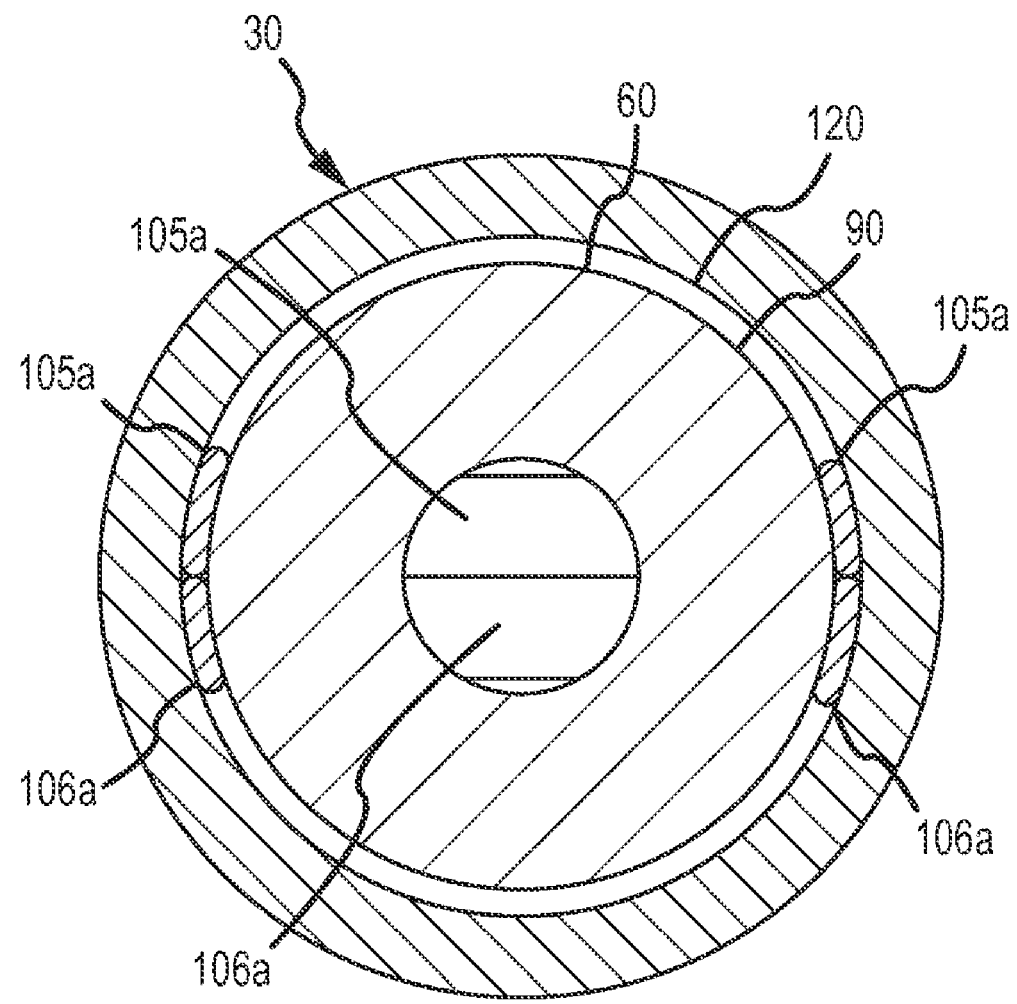
FIG. 6 is a cross-sectional view of FIG. 5 taken along the line 6-6.
Figure 7:
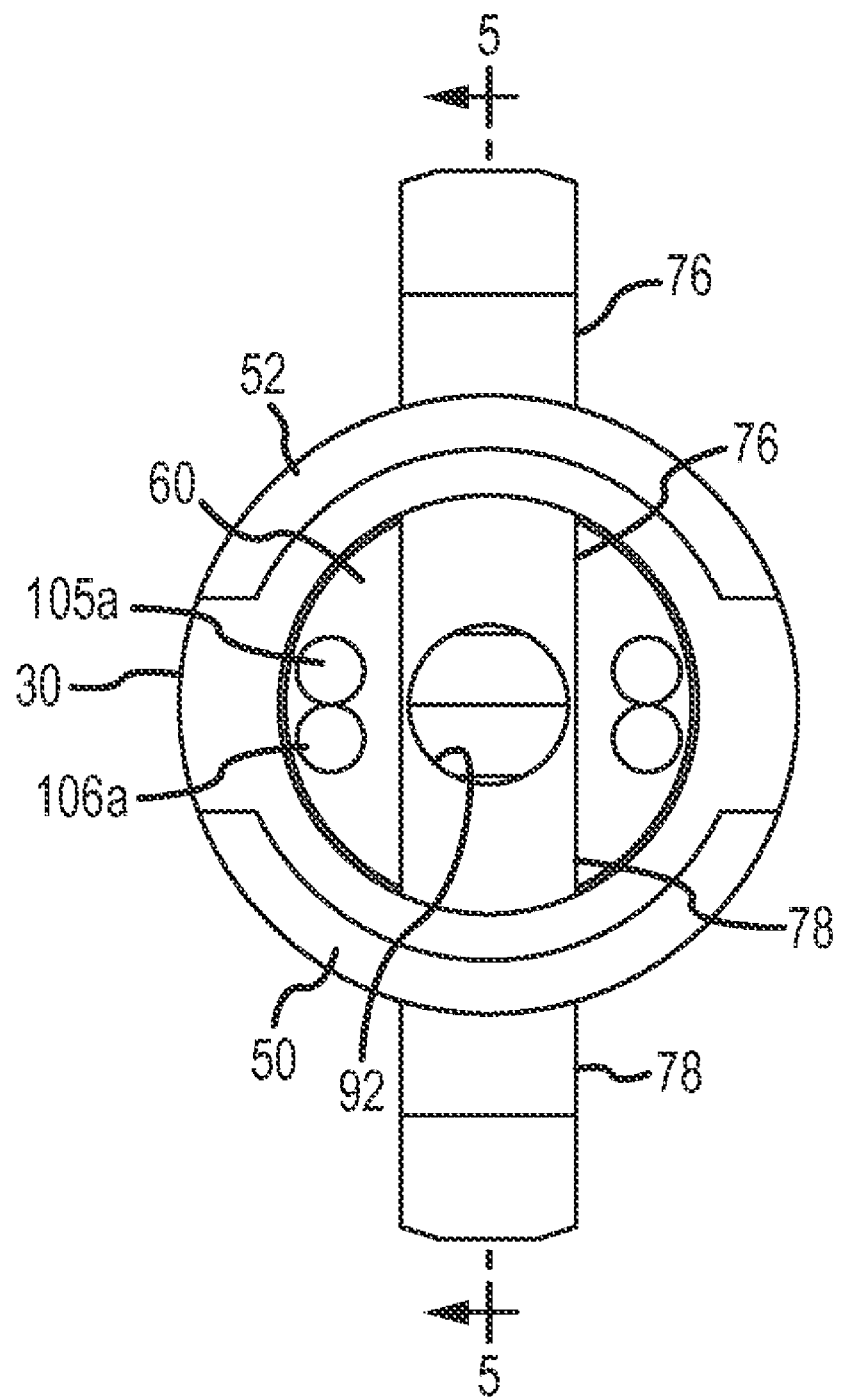
FIG. 7 is a right end view of FIG. 5.

Anchor 10 is initially manufactured and loaded onto inserter 12 in an undeployed and suture-unlocked position as shown in FIGS. 1-4. When it is acceptably positioned within a bone hole, and when a suture is acceptably situated within the anchor (as will be explained below), the anchor may be simultaneously deployed and placed into a suture-locked configuration as shown in FIGS. 5-7. As best seen in FIGS. 2 through 4, knotless suture anchor 10 comprises a generally cylindrical hollow outer member 30 having an axis 32, a hollow interior space 34 defining an axially aligned lumen 36, a proximal end 38 and a distal end 40. In order to engage the wall of the bone hole, outer member 30 is provided with radially outwardly extending projections 42 which, in the preferred embodiment take the form of annular ribs 44 extending substantially from proximal end 38 to distal end 40. Outer member 30 is further provided with two arcuate recesses 50 and 52 at its proximal end 38, the recesses intended to mate with arcuate tabs 53 and 54 at the distal end 20 of shaft 16 as will be understood below. Outer member 30 is also provided with diametrically opposed apertures 56 and 58 having distal ends 57 and 59, respectively. Apertures 56, 58 and ends 57, 59 are intended to cooperate with other elements of suture anchor 10 as will be understood below.

Knotless suture anchor 10 further comprises an elongated generally hollow inner member 60 situated within the lumen 36 of outer member 30 and itself having an axially aligned lumen 37. Inner member 60 comprises a generally cylindrical distal portion 62 and a generally cylindrical proximal portion 64. While inner member 60 is adapted to slidably fit within the lumen 36 of outer member 30 and is, therefore, considered for the purposes of this explanation to be generally cylindrical, it will be understood that proximal portion 64 primarily comprises discrete, longitudinally extending and radially expandable diametrically opposed prongs 76 and 78 having a predetermined arcuate dimension in a plane perpendicular to axis 32. Therefore, a portion of the cylindrical wall of portion 64 is removed to define the prongs. Prongs 76 and 78 are each provided with a proximal step or shoulder 80, 82 and a distal step or shoulder 84, 86, the function of which will be explained below. While the preferred embodiment utilizes two prongs 76, 78 it will be understood that any number of prongs may be suitable provided they clear the sutures, as will be understood below.

Distal portion 62 is provided with a transverse suture receiving channel or eyelet 70 and an axially aligned access aperture 72 which facilitates the manufacture of anchor 10. Additional eyelets 70 may be provided depending upon how many sutures are used. The eyelets also may be staggered longitudinally and rotationally along distal portion 62. Distal portion 62 is also provided with a cylindrical suture crimping projection 90 and an axially aligned threaded aperture 92. As will be explained below, crimping projection 90 is intended to squeeze the suture to be locked by the device against the opposing surface of the outer member and/or against a shoulder edge 120 formed on the interior surface of outer member 30. As will be further explained below, threaded aperture 92 is intended to receive the threaded distal end 94 of actuating shaft 96.

In the preferred embodiment, inner and outer members 30 and 60 are each made of biocompatible material which is sufficiently resilient to enable relative longitudinal and radial motion between them as explained below. One such material is polyetheretherketone although other metallic and non-metallic or polymeric materials may be suitable. A determining factor for suitability is the ability of the material to be momentarily deformed and to assume a final position with strength as anchor 10 transitions from an undeployed, suture-unlocked configuration to a deployed, suture-locked configuration. It will also be understood that the outer diameter of outer member 30 may be tapered distally and/or the depth of the annular channels between rib projections 42 may progressively decrease distally in order to facilitate pushing anchor 10 into a pre-formed bone hole.

In the configurations shown in FIGS. 1-4 knotless suture anchor 10 is shown as it is provided to the user, that is, in an undeployed and suture-unlocked configuration in order to facilitate assembly of suture anchor 10 with a suture to be knotlessly locked in place. The assembly process is facilitated by a suture loading mechanism best seen in FIGS. 2 and 3. Loading mechanism 100 comprises a handle 102 attached to a loop 104 of flexible material such as suture or any other suitable filamentary thread or the like. The suture loop 104 is formed of two legs 105 and 106 which are threaded through the suture anchor 10 and ultimately held within handle 102 of loading mechanism 100. Loop 104 and its constituent legs 105 and 106 follow a prescribed tortuous path from loop 104, on one side of the distal end 20 of inserter 12, to handle 102 situated on the diametrically opposite side of distal end 20. As shown by reference to FIGS. 2, 3 and 4, the tortuous path followed by constituent loop ends 105 and 106 is directed distally from loop 104 through outer member 30 via its open distal end 110, distally through lumen 36, distally around cylindrical crimping projection 90 within distal portion 62, transversely through transverse channel 70, proximally around cylindrical crimping projection 90, proximally through lumen 36, proximally out of the open end 110 of the outer member and into handle 102. It will be understood that the distal end of shaft 16 is provided with a pair of diametrically opposed cutouts 121 in order to enable loop constituent ends 105 and 106 to smoothly enter and exit open end 110 (and not protrude radially beyond the diameter of the bone hole). In the suture-unlocked position shown in FIGS. 2-4 the inner member 60 is positioned distally relative to outer member 30. Therefore, loop ends 105 and 106 are able to pass easily out of the distal end 107 of the outer member and past cylindrical crimping projection 90. Alignment line 122 is proximally extending to facilitate alignment of anchor 10 within the bone hole.

In use, loading or threading mechanism 100 is used to pull suture (to be used to secure tissue) along the same tortuous path as constituent loops ends 105 and 106. That is, as will be understood below, when a suture or plurality of sutures is intended to be knotlessly secured, the suture and/or plurality of sutures is passed through loop 104. Pulling handle 102 proximally toward handle 14 of inserter 12 will cause the loop 104 and consequently the suture to follow the same tortuous path described above ultimately resulting in removing the handle 102 and loop 104 from engagement with the suture anchor 10 and replacing it with the suture to be knotlessly secured. (When suture has been so positioned to replace ends 105 and 106, the numerals 105a and 106a will be used herein to designate suture as opposed to the loading loop ends 105 and 106).

As mentioned, FIGS. 1-4 show knotless suture anchor 10 in an undeployed and suture-unlocked position. In this position the inner member 60 is at its distal-most position relative to outer member 30 and any suture threaded through the tortuous path between the inner and outer members is able to freely slide along this path. Furthermore, the outer diameter of anchor 10 is substantially equal to the outer diameter of outer member 30 and the undeployed distance between the outer surfaces of prongs 76 and 78. This enables the anchor 10 to be positioned easily within a preformed bone hole prior to deploying or locking the anchor in place. The engagement of proximal steps 80 and 82 with end surfaces 57 and 59, respectively, helps keep anchor 10 in an undeployed configuration until the user is ready to deploy it.

Figure 8:
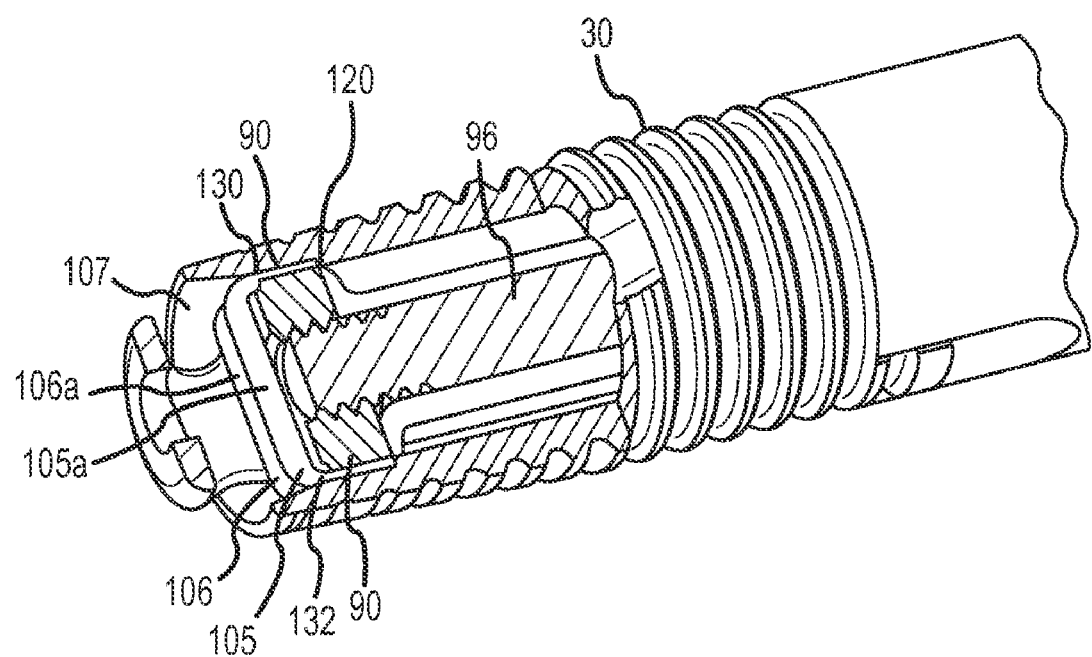
FIG. 8 is a front perspective cutaway view of FIG. 5 showing anchor 10 in a deployed and suture-locked configuration.
Figure 9:
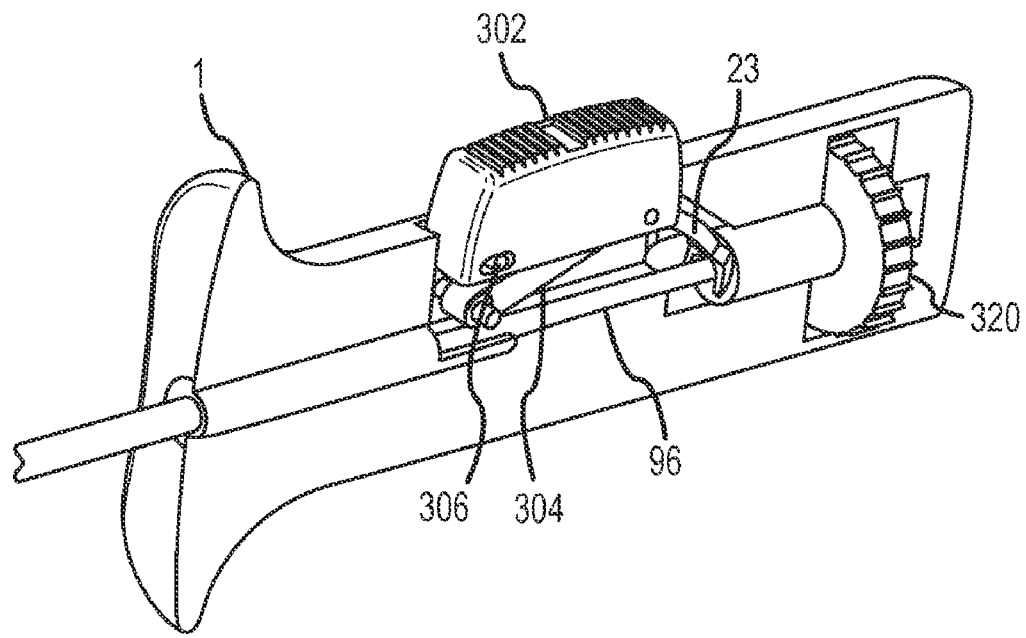
FIG. 9 is a front perspective schematic view of the handle portion of FIG. 1 in an undeployed position.
Figure 10:
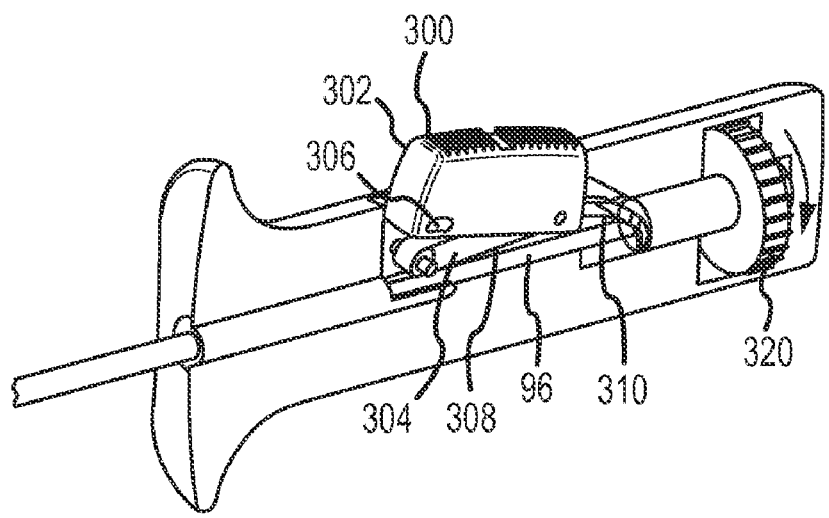
FIG. 10 is a view of FIG. 9 in a deployed position.

Anchor 10 is designed to be actuated by inserter 12 when a user decides it is properly positioned so that it can be deployed and placed in a suture-locked position. Such position is shown in FIGS. 5-8. The relationship of the various elements of anchor 10 in this deployed and suture-locked position is now going to be described, while the means by which it is placed in this configuration will be described below by reference to the operation of inserter 12 as shown in FIGS. 9 and 10. As shown in FIG. 5, when in the suture-locked position, inner member 60 is situated at its proximal-most position relative to outer member 30. This causes suture crimping projection 90 to compress suture ends 105a and 106a (which replaced the constituent loop ends 105 and 106) within gap 93 and against annular shoulder 120 (best seen in FIG. 8). Relatively simultaneously, as the inner member 60 is moved proximally relative to outer member 30, the distal ends 122 and 124 of prongs 76 and 78, respectively, contact ramp surfaces 126 and 128 situated at the distal ends of diametrically opposed apertures 56 and 58 thereby urging prongs 76 and 78 radially outwardly as best seen in FIG. 5 into the surrounding bone (not shown). When fully extended, prongs 76 and 78 will be held in such an extended position and prevented from moving distally by the engagement of distal steps 84 and 86 with aperture end surfaces 57 and 59, respectively. When extended, prongs 76 and 78 are intended to be situated within cancellous bone and under the cortical layer. It will be understood that FIG. 5 shows the components of anchor 10 in a cross-section taken in a plane parallel to prongs 76, 78 and perpendicular to the suture path. As a result, the compression of the suture is not shown in FIG. 5. After anchor 10 is deployed and set into the suture-locked configuration, inserter 14 may be disconnected from anchor 10 by unscrewing actuating shaft 96 from aperture 92 by unscrewing knob 320 at the proximal end of handle 14.

It will be understood that in the preferred embodiment dimensions and the tolerances of the inner and outer members 60, 30 are such that as the inner member moves proximally it and the suture it engages may deform the distal end of outer member 30 out of concentricity as the suture is crimped only at two diametrically opposed locations 130, 132 (best seen in FIG. 7). The locations spaced 90° from locations 130, 132, i.e. in the plane of prongs 76 and 78, are not subjected to the same stresses and may not be deformed to the same extent. The extent of the deformation is well within the degree of resilience of the material.

The method of using knotless suture anchor 10 and its operation is now best understood by reference to FIGS. 9 and 10 showing the manner in which inserter 12 is actuated. These method steps are performed when the user has properly passed suture through target tissue, inserted the anchor into a bone hole and applied sufficient tension to the suture to justify deploying the anchor. Inserter 12 is provided with an anchor actuating mechanism 300 comprising a trigger 302 and a drive mechanism 304 attached to the proximal end of actuating shaft 96. FIG. 9 shows the positions of components prior to actuation and FIG. 10 shows the positions after actuation. Shaft 96 is axially aligned within and movable relative to shaft 16 and its distal end 94 is threaded into aperture 92 within the distal portion 62 of inner member 60. The distal end of shaft 16 is provided with tabs 53 and 54 which are received within recesses 50 and 52 of the outer member 30. The tabs and recesses operate together to prevent anchor 10 from either rotating or moving proximally relative to shaft 16. Trigger 302 is pivotably mounted on pivot 306 and is attached to levers 308 and 310. The distal end of lever 308 is fixed relative to handle 14 and the proximal end of lever 310 is fixed relative to actuating shaft 96. Depressing trigger 302 exerts a proximally directed force on the proximal end of actuating shaft 96 which in turn pulls inner member 60 proximally relative to outer member 30. This action simultaneously puts anchor 10 into the deployed configuration, with expanded prongs 76, 78 best seen in FIG. 5, and into the suture-locked configuration, with the suture crimped within the tortuous path as best seen in FIG. 8.

Figure 11:
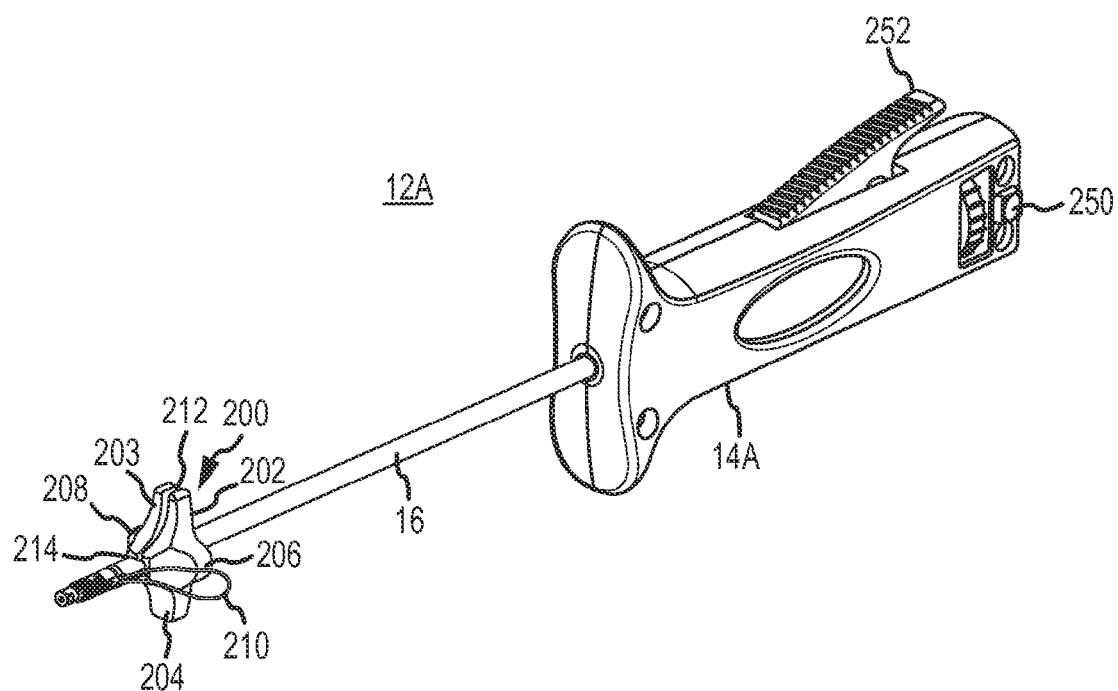
FIG. 11 is a front perspective view of an alternate embodiment of FIG. 1.

An alternate embodiment of the inserter and loading mechanism used with knotless suture anchor 10 is shown in FIG. 11 and designated as inserter 12A having a loading mechanism 200 and a handle 14A. The only substantial difference between handle 14 (FIG. 1) and handle 14A is the addition in the latter of a safety trigger 250. Trigger 250 is attached to the proximal end of actuating shaft 96 in order to prevent any premature and unintended actuation or rotation anchor 10. Trigger 250 prevents the loading mechanism from exerting any proximally directed force on inner member 60 as loop 104 and any sutures threaded through the loop are pulled through the tortuous path described above. After the suture has been loaded appropriately, trigger 250 may be depressed or otherwise activated in order to enable trigger 252 (substantially identical to trigger 302 of FIGS. 9 and 10) to be actuated.

FIG. 11 also shows an alternative embodiment of a suture loading mechanism 200 in the form of a handle 202 comprising a pair of diametrically opposed finger tabs 203 and 204, a loop retaining slot 206 and an engagement tab 208 for securely holding the ends of loop 210. Loading mechanism 200 is provided with a split gap 212 extending from a central aperture 214 adapted to frictionally engage the outer surface of shaft 16. In use, when a suture is threaded through loop 210, a user may pull on finger tabs 203, 204 to easily slide handle 202 proximally along shaft 16. Mechanism 200 thus incorporates a suture threader retaining mechanism onto anchor inserter 12A.

Figure 12:
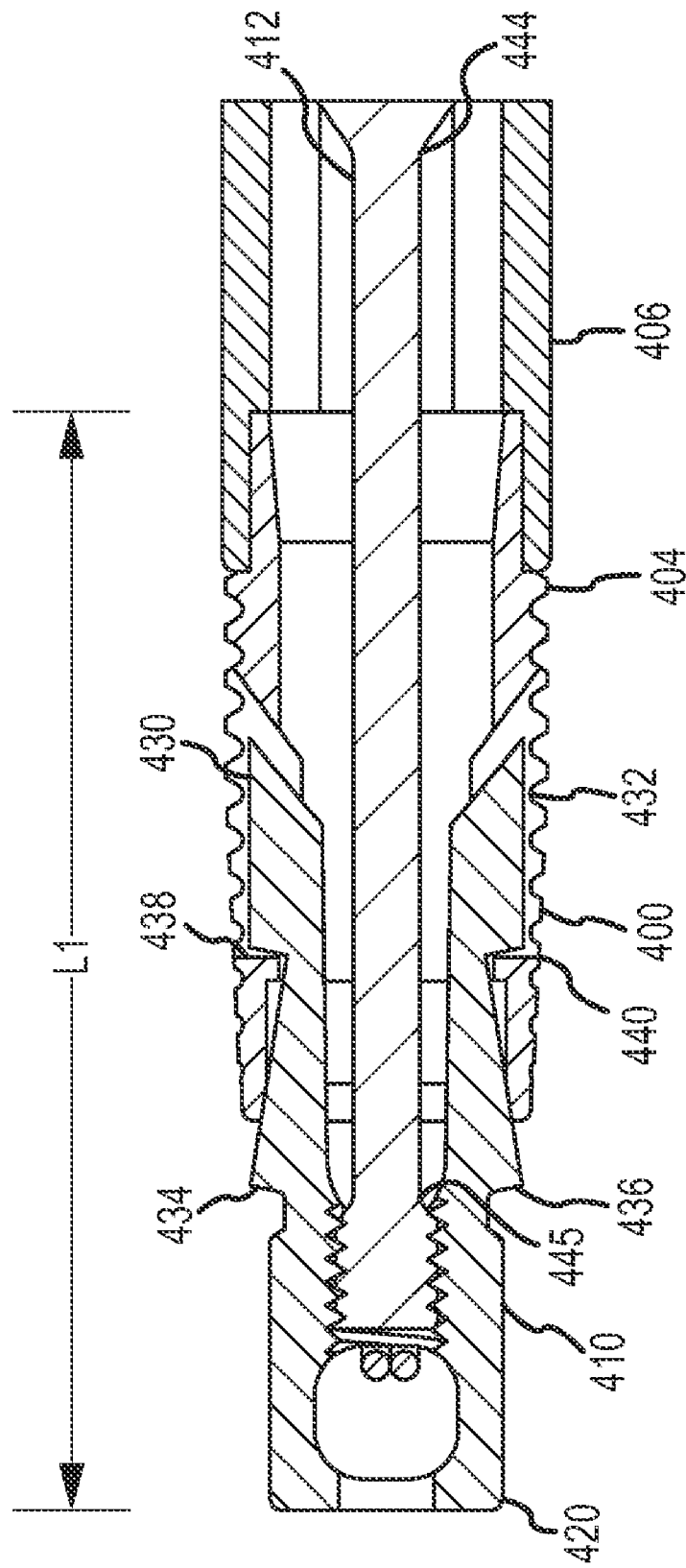
FIG. 12 is a cross-sectional view of an alternate embodiment of the knotless suture anchor of FIGS. 1-5 shown in an undeployed and suture-unlocked position.
Figure 13:
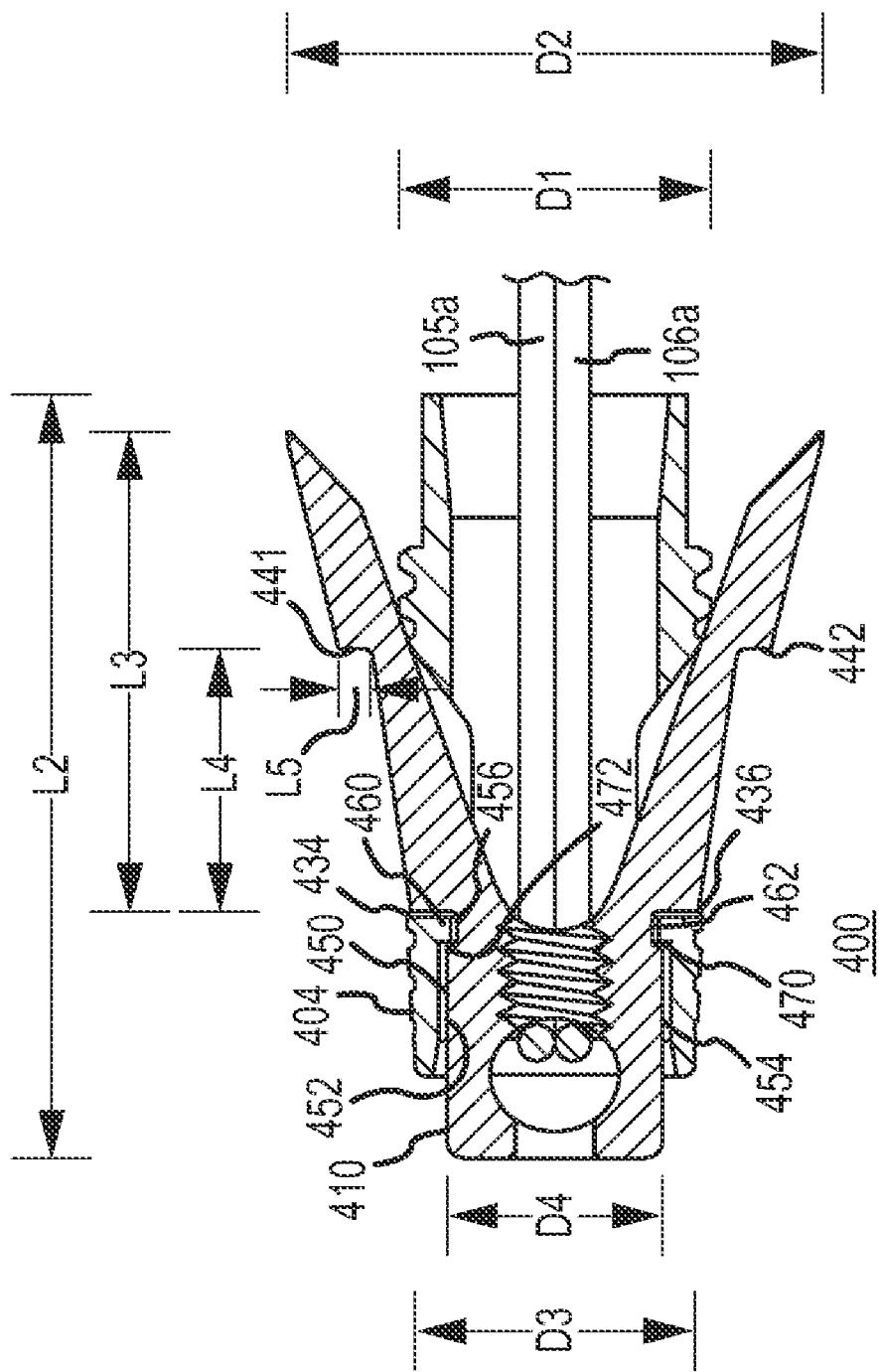
FIG. 13 is a view of FIG. 12 in a deployed and suture-locked position.

An alternate embodiment of anchor 10, designated with the numeral 400, is shown in undeployed and deployed configurations in FIGS. 12 and 13, respectively. Anchor 400 comprises outer member 404 attached to the distal end of an inserter shaft 406 substantially the same as outer member 30 and shaft 16 of FIG. 4. Inner member 410 and actuating shaft 412 are similar to inner member 60 and shaft 96 of FIG. 4 but differ in at least the following ways. Inner member 410 has a cylindrical distal end 420 having the same diameter along its length, thereby eliminating the relatively short cylindrical crimping projection 90 of anchor 10. Prongs 430, 432 are formed with steps 434, 436 which are tapered a predetermined amount proximally (on the order of 2-3 degrees) so that when the prongs are deployed, the surfaces of steps 434, 436 are more likely to lie parallel to the surface of aperture end surfaces 438 and 440, respectively, as best seen in FIG. 13. Proximal steps 441 and 442 may also be tapered. The diameter of actuating shaft 412 is decreased between points 444 and 445 in order to provide more clearance for prongs 430 and 432 as they flex inwardly and outwardly as inner member 410 is moved proximally relative to outer member 404.

As shown in FIG. 13, anchor 400 produces an annular crimping gap 450 between the inner annular surface 452 of outer member 404 and the outer annular surface 454 of inner member 410. This crimping gap 450 extends longitudinally along the length of surface 452 where it is substantially parallel to surface 454. Similarly to anchor 10, anchor 400 also produces interacting edges and a tortuous suture path by virtue of the gap 456 between annular flange 460 of outer member 404 and annular recess 462 of inner member 410 and the transition/shoulder edge 470 between gap 450 and gap 456. The proximal rim/shoulder 472 of surface 454 and the distal rim/shoulder 470 of flange 460 further constrict any movement of the suture passing between these rims. Rim 472 exerts a proximally directed force on the suture while rim 440 exerts a distally directed force.

In the preferred embodiment in FIGS. 12 and 13 made from polyetherehterketone, the length L1 of undeployed anchor 400 is preferably in the range of 12 to 17 mm and the deployed length L2 is in the range of 9 to 11 mm. The length L3 of prongs 430 and 432 is on the order of 4 to 10 mm, with the length L4 between steps 434 and 441, and steps 436 and 442 being in the range of 2 to 5 mm. The length L5 of each step is on the order of 0.2 to 0.7 mm. The undeployed diameter D1 at the proximal end of the anchor is on the order to 4 to 6 mm and the deployed diameter is on the order to 6 to 9 mm. The diameter D3 at the distal end of the outer member is on the order to 3 to 5 mm while the diameter D4 of the distal end of the inner member is on the order of 2-4 mm. The size of gap 450 is on the order of 0.1 mm which has been found acceptable when used with size 2 multi-filament suture having a diameter of 0.5-0.630 mm. Changes in these various dimensions may be made depending upon the composition, type and size of suture to be used.

Figure 14:
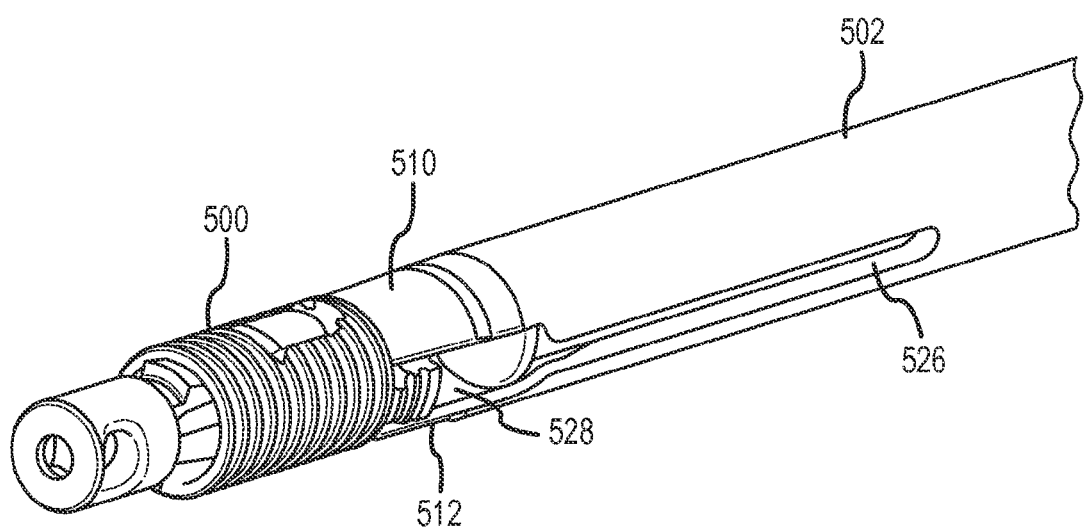
FIG. 14 is a front perspective view of an alternate embodiment of the invention.
Figure 15:
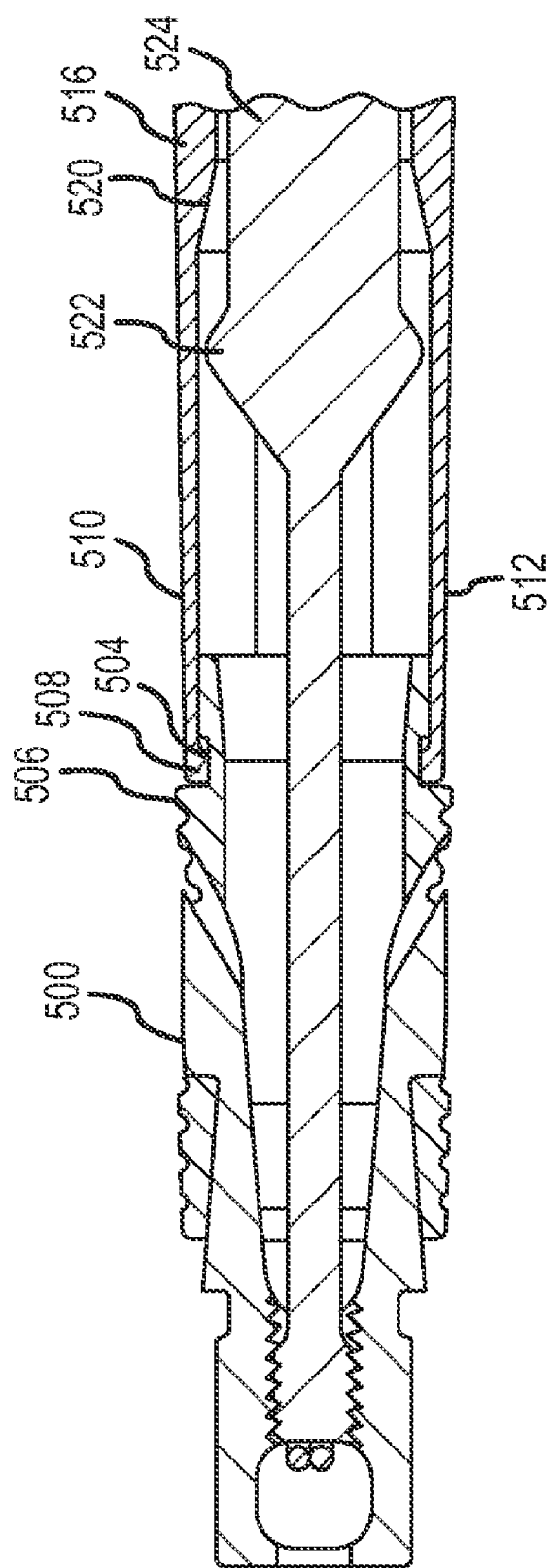
FIG. 15 is a cross-sectional view of FIG. 14 in an undeployed configuration.
Figure 16:
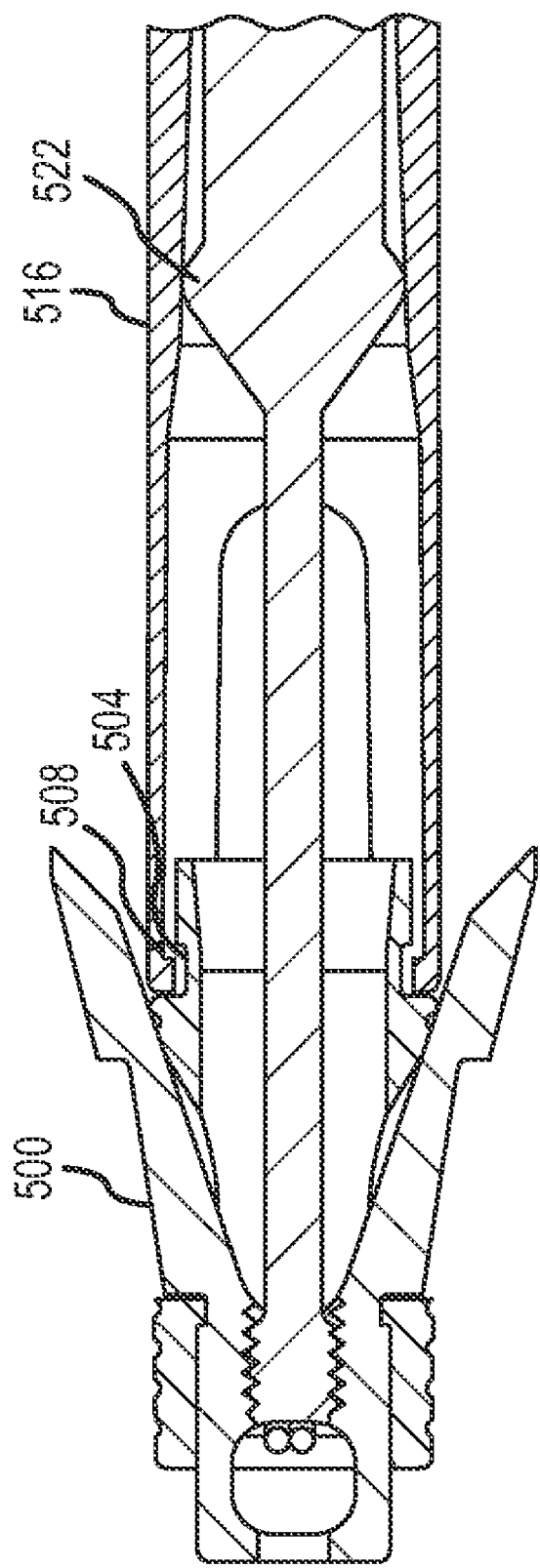
FIG. 16 is a view of FIG. 15 in a deployed, suture-locked configuration.

Another embodiment of the invention is shown in FIGS. 13-15 as anchor 500 and associated inserter 502. The only difference between anchor 500 and the other embodiments is the inclusion of a shallow annular groove 504 at the distal end of outer member 506 and a corresponding inwardly extending annular rib 508 on arcuate tabs 510 and 512 of inserter shaft 516. Shaft 516 is also provided with an annular inwardly extending ramp 520 situated proximally of expansion rib 522 outwardly extending from actuating shaft 524. Tabs 510 and 512 are able to flex by virtue of diametrically opposed slots 526 extending from suture clearance slots 528. This modification provides security in the use of anchor 10 by preventing premature distal movement of outer member 506 and accidental/unintended deployment of anchor 500. Rib 508 and groove 504 prevent the outer member from disengaging from shaft 516 until its arcuate tabs 510, 512 are pushed radially outwardly by expansion rib 522 when actuating shaft 524 is moved proximally.

It will be understood by those skilled in the art that numerous improvements and modifications may be made to be preferred embodiment of the invention disclosed herein without departing from the spirit and scope thereof.

What is claimed is:

1. A knotless suture anchor comprising:
    a generally cylindrical, hollow outer member having an axial first lumen, an outer surface, a distal end and a proximal end;
    an elongated, generally hollow inner member having an axial second lumen being an axially aligned central cavity defined at least in part by a generally cylindrical proximal portion and having a transverse passage defined by a distal portion for receiving suture therethrough, said inner member adapted to move longitudinally within said outer member between a distal, suture-unlocked position and a proximal, suture-locked position;
    a suture directed along a path distally through said first and second lumens, transversely through said transverse passage, and proximally through said first and second lumens;
    a suture-locking means situated along said path proximally of said transverse passage, said suture-locking means comprising at least one crimping area interposed between said inner and outer members, said crimping area being normally situated in a suture-unlocked configuration wherein said inner member is situated distally relative to said outer member so said suture is slidable along said path, said crimping area adapted to be activated into a suture-locked configuration upon proximal movement of said inner member relative to said outer member;
    means for moving said inner member proximally from said suture-unlocked position to said suture-locked position wherein said suture is crimped between said inner and outer members; and
    means for locking said inner member to said outer member to maintain said inner member in said suture-locked position.

2. A knotless suture anchor according to claim 1 wherein said suture-locking means further comprises:
    a distally directed suture-locking shoulder formed at the distal end of said first lumen of said outer member;
    a proximally directed suture-locking shoulder formed on the distal portion of said inner member, said shoulders adapted to crimp suture between them.

3. A knotless suture anchor according to claim 1 further comprising an elongated activating shaft means for moving said inner member longitudinally, said shaft means comprising a shaft extending through said first and second lumens and detachably secured to said inner member.

4. A knotless suture anchor according to claim 1 further comprising radially outwardly extending projections on said outer surface of said outer tubular member for engaging bone.

5. A knotless suture anchor according to claim 1 wherein said suture comprises a loop with both ends of said loop extending into, across and out of said inner member before, during and after its movement from said suture-unlocked position to said suture-locked position.

6. A knotless suture anchor according to claim 1 wherein said locking means is further adapted to extend radially outwardly of said outer surface.

7. A knotless suture anchor according to claim 1 wherein said means for locking comprises a first distal facing shoulder provided on an external surface of said inner member and a first proximal facing shoulder provided on said outer member, said first distal facing shoulder engaging with said proximal facing shoulder in said suture-locked position.

8. A knotless suture anchor according to claim 7, wherein said first distal facing shoulder is provided on a first prong portion of said inner member, said first prong portion extending through a first aperture provided through said outer member in said suture-locked position, said first proximal facing shoulder defining a distal extent of said first aperture.

9. A knotless suture anchor according to claim 8 further comprising: a first outer member ramp defining a proximal extent of said first aperture; and a first inner member ramp provided at a proximal extent of said first prong portion, wherein said first inner member ramp engages said first outer member ramp at least during a transition between said suture-unlocked position and said suture-locked position.

10. A knotless suture anchor according to claim 9 further comprising: a second prong provided on said inner member opposite said first prong, said second prong comprising a second distal facing shoulder corresponding to said first distal facing shoulder; and a second aperture provided through said outer member opposite said first aperture, a distal extent of said second aperture being defined by a second proximal facing shoulder.

11. A knotless suture anchor according to claim 10 further comprising: a third distal facing shoulder provided on said first prong portion inner member at a location proximal to said first distal facing shoulder; and a fourth distal facing shoulder provided on said second prong portion, wherein said third distal facing shoulder engages said first proximal facing shoulder and said fourth distal facing shoulder engages said second proximal facing shoulder in said suture-unlocked position.

12. A knotless suture anchor according to claim 9 further comprising a third distal facing shoulder provided on said first prong portion at a location proximal to said first distal facing shoulder, said third distal facing shoulder engaging said first proximal facing shoulder in said suture-unlocked position.

13. A knotless suture anchor comprising:
- a hollow outer member having a suture-locking annular surface at its distal end;
- a hollow inner member slidable within said outer member and having a suture-locking annular projection at its distal end;
- a suture extending along a path extending between said suture-locking annular surface and said suture-locking annular projection and through said outer member;
- said inner member movable between a suture-unlocked position wherein said suture is slidable along said path and wherein said suture-locking annular projection is longitudinally spaced from said suture-locking annular surface, and a suture-locked position wherein said suture-locking annular surface and said suture-locking annular projection are secured sufficiently near each other to crimp said suture therebetween; and
- means for locking said inner member to said outer member to maintain said inner member in said suture-locked position comprising a first distal facing shoulder provided on an external surface of said inner member and a first proximal facing shoulder provided on said outer member, said first distal facing shoulder engaging with said proximal facing shoulder in said suture-locked position,
- wherein said first distal facing shoulder is provided on a first prong portion of said inner member, said first prong portion extending through a first aperture provided through said outer member in said suture-locked position, said first proximal facing shoulder defining a distal extent of said first aperture.

14. A knotless suture anchor according to claim 13 further comprising: a first outer member ramp defining a proximal extent of said first aperture; and a first inner member ramp provided at a proximal extent of said first prong portion, wherein said first inner member ramp engages said first outer member ramp at least during a transition between said suture-unlocked position and said suture-locked position.

15. A knotless suture anchor according to claim 14 further comprising: a second prong provided on said inner member opposite said first prong, said second prong comprising a second distal facing shoulder corresponding to said first distal facing shoulder; and a second aperture provided through said outer member opposite said first aperture, a distal extent of said second aperture being defined by a second proximal facing shoulder.

16. A knotless suture anchor according to claim 15 further comprising: a third distal facing shoulder provided on said first prong portion inner member at a location proximal to said first distal facing shoulder; and a fourth distal facing shoulder provided on said second prong portion, wherein said third distal facing shoulder engages said first proximal facing shoulder and said fourth distal facing shoulder engages said second proximal facing shoulder in said suture-unlocked position.

17. A knotless suture anchor according to claim 14 further comprising a third distal facing shoulder provided on said first prong portion at a location proximal to said first distal facing shoulder, said third distal facing shoulder engaging said first proximal facing shoulder in said suture-unlocked position.

* * * * *